(12) United States Patent
Matsumoto et al.

(10) Patent No.: US 6,872,708 B2
(45) Date of Patent: Mar. 29, 2005

(54) LOCAL INJECTION PRESCRIPTION

(76) Inventors: Mitsukazu Matsumoto, 57-9, Ikehata 3-chome, Chiryu-shi, Aichi 472-0025 (JP); Hisatake Ishikawa, 2-28, Tokugawayamacho 6-chome, Chikusa-ku, Nagoya-shi, Aichi 464-0031 (JP); Hirohiko Matsumoto, 57-9, Ikehata 3-chome, Chiryu-shi, Aichi, 472-0025 (JP)

( * ) Notice: Subject to any disclaimer, the term of this patent is extended or adjusted under 35 U.S.C. 154(b) by 0 days.

(21) Appl. No.: 10/409,441

(22) Filed: Apr. 7, 2003

(65) Prior Publication Data

US 2003/0207822 A1 Nov. 6, 2003

Related U.S. Application Data

(63) Continuation-in-part of application No. 09/954,513, filed on Sep. 10, 2001, now abandoned.

(51) Int. Cl.[7] ............................................. A61K 31/70
(52) U.S. Cl. ......................................................... 514/30
(58) Field of Search ...................................... 514/30, 28

(56) References Cited

U.S. PATENT DOCUMENTS

| 5,686,274 A | 11/1997 | Ali | ............................... 435/125 |
| 6,617,304 B1 * | 9/2003 | Aoki et al. | .................... 512/11 |
| 6,617,314 B2 * | 9/2003 | Grosse-Bley et al. | .......... 514/28 |
| 6,720,302 B2 * | 4/2004 | Frerot et al. | ................... 512/25 |
| 6,720,327 B2 * | 4/2004 | Ruminski et al. | ............ 514/269 |
| 6,746,818 B2 * | 6/2004 | Kinsho et al. | ............ 430/270.1 |

FOREIGN PATENT DOCUMENTS

| JP | H5-7371 | 1/1993 |
| WO | WO93/18652 | 9/1993 |
| WO | WO93/18653 | 9/1993 |

OTHER PUBLICATIONS

Patent Abstracts of Japan, Publication No. 04222595 A, Published Aug. 12, 1992.

Nishio et al., "Antitumor Effects of Butyrolactone I, a Selective cdc2 Kinase Inhibitor, on Human Lung Cancer Cell Lines," (1996) Anticancer Research 16, pp. 3387–3388.

Mazurkiewicz, et al., "GABA Level and GAD Activity in Human and Mouse Normal and Neoplastic Mammary Gland," (1999) J. Exp. Clin. Cancer Res., 18, 2, pp. 247–253.

* cited by examiner

*Primary Examiner*—Elli Peselev
(74) *Attorney, Agent, or Firm*—Beyer Weaver & Thomas LLP

(57) ABSTRACT

A local injection prescription that disperses a malignant tumor to decrease the size of the tumor or terminate the tumor. The local injection prescription is produced by dissolving an organic compound having a lactone nucleus in lower alcohol and water.

11 Claims, No Drawings

LOCAL INJECTION PRESCRIPTION

REFERENCE TO PRIOR APPLICATION

This application is a continuation-in-part and claims the benefit of prior U.S. application Ser. No. 09/954,513 filed Sep. 10, 2001, now abandoned.

BACKGROUND OF THE ART

The present invention relates to a prescription prepared for local injections to treat malignant tumors that are commonly seen in birds and mammals.

The general approach for treating a malignant tumor is to incise the lesion or administer an anti-tumor preparation. However, the incision of the lesion to treat cancer may result in contraction of the portion surrounding the lesion and formation of a cicatrix. In such case, the portion surrounding the lesion does not heal properly and form the same healthy tissues as those prior to the incision. The administration of an anti-tumor preparation is performed to basically prevent the enlargement and spreading of the tumor. In this case, it is difficult for the anti-tumor preparation to act directly on the tumor and decrease the size of the tumor or terminate the tumor.

SUMMARY OF THE INVENTION

Accordingly, it is an object of the present invention to provide a local injection prescription that disperses a malignant tumor to decrease the size of the tumor or terminate the tumor by directly injecting the prescription to the lesion.

To achieve the above object, the present invention provides a local injection prescription obtained by dissolving an organic compound, which has a lactone nucleus, in lower alcohol and water. The organic compound contains macrolide. Macrolide includes avermectin.

Further, the organic compound includes phenytoin.

The lower alcohol is an alcohol selected from a group of alcohols represented by the molecular formulas of $CH_4O$, $C_2H_6O$, $C_3H_8O$, and $C_4H_{10}O$.

Lactone is a substance defined as an anhydride of hydroxy acid. Further, lactone is dehydrated and condensed to form the lactone nucleus. Macrolide is one example of an organic compound having the lactone nucleus. Macrolide is the generic term for substances that have a frame using a large lactone nucleus as a chemical structure. Further, macrolide is often included in antibiotics obtained from actinomycetes. Avermectin is one type of macrolide. Natural avermectin is obtained by fermenting actinomycete *streptomyces* avermitilis. Ivermectin is a widely known avermectin and is 2, 2, 2, 3-dihydroavermectin B1.

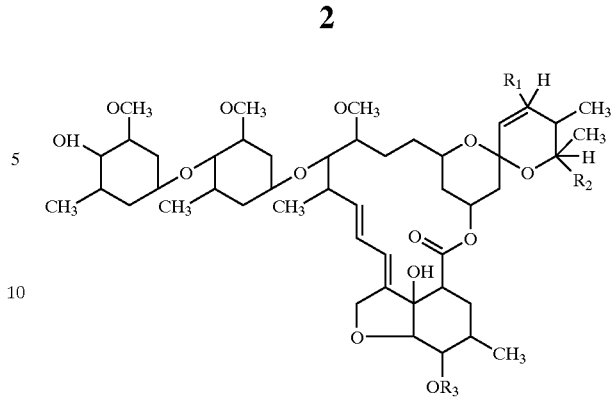

TABLE 1

|  | R1 | R2 | R3 |
|---|---|---|---|
| A1a |  | C2H5 | CH3 |
| A1b |  | CH3 | CH3 |
| A2a | OH | C2H5 | CH3 |
| A2b | OH | CH3 | CH3 |
| B1a |  | C2H5 | H |
| B1b |  | CH3 | H |
| B2a | OH | C2H5 | H |
| B2b | OH | CH3 | H |

The administration of macrolide as a substance having the lactone nucleus has shown that macrolide has an anti-tumor feature (Japanese Patent Publication Nos. 7-504913 and 7-504914). However, these observations have not focused on local usage. Although, it may be presumed that the local usage of macrolide as a substance having the lactone nucleus is effective, there have been no prescriptions for macrolide. It is possible to solely use a substance having the lactone nucleus. It is also possible to combine and use two or more substances having the lactone nucleus.

It is preferred that the lower alcohol be monatomic alcohol. Diatomic and triatmoic have high viscosity under normal temperatures and can thus not be solely used. It is further preferred that the monatomic alcohol be one of $C_1$ to $C_4$. It is especially preferred that the lower alcohol be methyl alcohol ($CH_4O$) and ethyl alcohol ($C_2H_6O$), which have small molecular weights. Although methyl alcohol may be used, the most preferred lower alcohol is ethyl alcohol since the amount used for local injections is small. Since the molecular weight of lower alcohol is small, lower alcohol easily passes through cell membranes. Further, since alcohol has a hydrophilic group and a hydrophobic group, alcohol may be used as a solvent that easily dissolves a substance having the lactone nucleus such as ivermectin. Additionally, alcohol easily permeates portions of cells having a high water content. In addition, ethanol is administered to treat hepar cancer. This is because alcohol inactivates glycogen, which is the energy source for growing cancer cells. Accordingly, alcohol is optimal for use as a prescription in the present invention.

However, the usage of ethyl alcohol having a high purity is painful when the ethyl alcohol permeates cells. It is thus preferred that the ratio of ethyl alcohol be 35 to 70 weight by percent. Once the alcohol permeates cells, pain is eliminated due to the peripheral nervous system blocking effect.

It is preferred that α-amino acid be mixed with the prescription that is prepared in this manner. A functional group of α-amino acid is represented by the following expression.

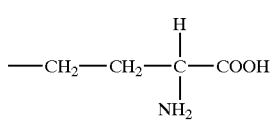

Examples of α-amino acid are aminobutyric acid, glutamic acid, and theanine. For example, L-aminobutyric acid is represented by the following expression.

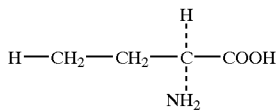

The broken lines indicate that the coupling group relative to carbon (C) is located in a direction downward from the plane of the drawing. The same applies hereafter.

From several observations related to antagonism of L-γ-amino acid having tropism with the GABA receptor of a suppressive nerve cell, it may be assumed that the similar L-α-amino acid has a function that enhances the division of cells. Although this function has not yet been completely understood, it may be assumed that L-α-amino acid suppresses the internal respiration effect of a nerve cell and induces apoptosis. Thus, the local use of L-α-amino acid on a malignant tumor enhances the apoptosis of nerve cells. Further, there have been observations that glutamic acid enhances apoptosis as it stagnates at synapse gaps. Thus, the applicant has prescribed α-amino acid, especially, theanine, which has the above functional group, to treat malignant tumors.

Theanine mainly refers to L-theanine and is represented by the following expression as a chemical substance, which is indicated by γ-ethylamino-L-glutamine.

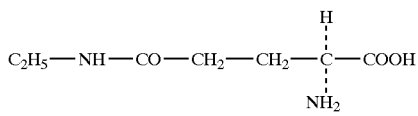

Theanine is a white crystalline powder known as one of the umami components of tea and has no smell. Further, theanine has been observed as preventing high blood pressure and preventing necrosis of cells due to ischemia.

Glutamic acid is mainly α-amino acid, which is widely known as umami component. For example, Glutamic acid is represented by the following expression.

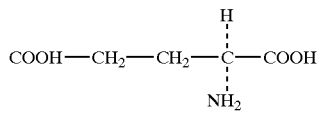

It is preferred that vitamin B6 be mixed with the prescription that is prepared in this manner.

The prescription according to the present invention is used to treat malignant tumors that are commonly seen in birds and mammals. Malignant tumors include sarcoma, adenoma, skin cancer, and the like. Further, mammals include humans.

DETAILED DESCRIPTION OF THE PREFERRED EMBODIMENT

A preferred embodiment according to the present invention will now be discussed. In the preferred embodiment, IVOMEC (registered trademark of Merial Ltd.) injection, which is used as an anti-parasite preparation, was used as an ivermectin preparation. The preparation includes 10 mg of ivermectin in 1 ml.

Further, 70 percent ethyl alcohol was used as a solvent.

The solubility of IVOMEC injection and ALEVIATIN injection liquid relative to water and 70 percent ethyl alcohol solution was as shown in the following table.

Table 2

| IVOMEC Injection | Ethyl Alcohol (70% Solution) | Water | Dissolubility |
|---|---|---|---|
| 1 | 1 | | ◉ |
| | 1 | | ◉ |
| 1 | 1 | | ◉ |
| 1 | | 1 | Δ |
| | | 1 | ○ |
| 1 | 1 | | ◉ |
| 1 | 1 | 1 | ◉ |
| 1 | | | ▲ |

◉: Dissolved
○: Mostly Dissolved
Δ: Turbid
▲: Viscous
※1 indicates that 1 cc was added and agitated.
The Solution was then left in a quiet state.

Prescription 1, which is described below, was used in example 1.

| Prescription 1 | |
|---|---|
| IVOMEC injection | 33.33 volume percent |
| 70 percent ethyl alcohol solution | 66.66 volume percent |

In example 2, as a basic prescription, the above prescription 1 was mixed with prescription 2, which is described below, and prescription 3 was mixed as required. In prescription 3, pyridoxine chloride was used as vitamin B6. Further, prescription 4 was used when necessary. Estrogen was also used since it is known to be especially effective on tumors near the anus of a male dog dipropionic acid estradiol was used as the estrogen.

| Prescription 2 | |
|---|---|
| L-theanine | 33.33 volume percent |
| 35 percent ethyl alcohol solution | 66.66 volume percent |

Prescription 3
1 ml ampul containing 10 mg of pyridoxine chloride (vitamin B6)
Prescription 4
1 ml ampul containing 5 mg of dipropionic acid estradiol as an estrogen
In the following examples, the prescriptions were all directly injected to the lesion.

EXAMPLE 1

(No. 1)
Prescription 1 was locally injected to treat anus tumor in a large-size dog (male, weighing about 17 kg). An amount of 1.0 cc per injection was administered once a month for a total of six times. The observations were as shown in Table 3.

(No. 2)

Prescription 1 was locally injected to treat mastadenoma and melanoma in a medium-size dog (female, weighing about 13 kg). An amount of 1.0 cc per injection was administered once a month for a total of three times to the mastadenoma. An amount of 1.0 cc per injection was administered once to the melanoma. The observations were as shown in Table 3.

(No. 3)

Prescription 1 was locally injected to treat vaginal sarcoma in a medium-size dog (female, weighing about 10.5 kg). A total of 0.9 cc, 0.3 cc for each of three locations in the sarcoma, was injected and administered once a month for a total of two times. The observations were as shown in Table 3.

(No. 4)

Prescription 1 was locally injected to treat mastocytoma formed near the groin at the right rear leg in a large-size dog (male, weighing about 22 kg). An amount of 1.0 cc per injection was administered once a month for a total of two times. The observations were as shown in Table 3.

(No. 5)

Prescription 1 was locally injected to treat malignant skin histoma formed near the outer side of the left hip in a small-size dog (female, weighing about 4 kg). An amount of 0.2 cc per injection was administered once a month for a total of two times. The observations were as shown in Table 3.

(No. 6)

Prescription 1 was locally injected to treat subcutaneous lymphoma formed in the back of a small-size dog (female, weighing about 3 kg). An amount of 0.2 cc was injected and administered once a month for a total of two times. The observations were as shown in Table 3.

(No. 7)

Prescription 1 was locally injected to treat the right mammary gland for mastadenoma in a large-size dog (female, weighing about 20 kg). The prescription was injected at three locations of the sarcoma. An amount of 0.5 cc was injected at each of the three locations totaling to 1.5 cc per administration once a month for a total of two times. The observations were as shown in Table 3.

(No. 8)

Prescription 3 was locally injected to treat multiple skin cancer and chondrosarcoma of the entire body and the 16th rib in a large-size dog (male, weighing about 18 kg). An amount of 1.0 cc per injection was administered once a month for a total of two times to treat the multiple skin cancer. An amount of 1.0 cc per injection was administered once a month for a total of three times to treat the chondrosarcoma. The observations were as shown in Table 3.

(No. 9)

Prescription 1 was locally injected to treat osteosarcoma in the rear left femur of a medium-size dog (male, weighing about 15 kg). An amount of 1.0 cc per injection was administered once. The observations were as shown in Table 3.

(No. 10)

Prescription 1 was locally injected to treat folliculus pili cellular tumor in the neck and left back-side hip of a large-size dog. An amount of 0.5 cc was injected to the sarcoma at one location and an amount of 0.7 cc was injected to the sarcoma at another location. A total of 1.5 cc was administered once a month for a total of two times. The observations were as shown in Table 3.

(No. 11)

Prescription 1 was locally injected to treat upper jaw sinus sarcoma of the nasal cavity upper jaw sinus in a cat (male, weighing about 3 kg). An amount of 0.5 cc per injection was administered once a month for a total of three times. The observations were as shown in Table 3.

(No. 12)

Prescription 1 was locally injected to treat lymphoma of the rear right groin in a small-size dog (male, weighing about 5 kg) once. The observations were as shown in Table 3.

TABLE 3

| No. | Observation Results |
| --- | --- |
| 1 | Completely healed |
| 2 | Both completely healed |
| 3 | Completely healed |
| 4 | Completely healed |
| 5 | Completely healed |
| 6 | Completely healed |
| 7 | Reduced to ⅔ in first month |
| 8 | Both completely healed |
| 9 | Completely healed |
| 10 | Completely healed |
| 11 | Reduced to ½ in fourth month |
| 12 | Reduced to ½ in first month |

EXAMPLE 2

(No. 1)

A 1 ml ampul of prescription 4 was locally injected to an anus tumor of a middle-size dog (male, weighing about 12 kg). An ampul of prescription 4 mixed with equally mixed prescriptions 1 and 3 was also locally injected. A total amount of 19 ml, which consists of 4.5 ml of prescription 1, 4.5 ml of prescription 3, and 10 ml of prescription 4, per injection was administered once every month for a total of two times. The observations were as shown in Table 4.

(No. 2)

A 0.8 ml ampul of prescription 4 was locally injected to an anus tumor of a middle-size dog (male, weighing about 12 kg). An ampul of prescription 4 mixed with equally mixed prescriptions 1 and 3 was also locally injected. A total amount of 13 ml, which consists of 1.5 ml of prescription 1, 1.5 ml of prescription 3, and 10 ml of prescription 4, per injection was administered once every month for a total of three times. The observations were as shown in Table 4

(No. 3)

An ampul of prescription 4 was mixed with equally mixed prescriptions 1 and 3 and locally injected to an adiposis cell tumor of a large-size dog (male, weighing about 27 kg). A total amount of 15 ml, which consists of 2.5 ml of prescription 1, 2.5 ml of prescription 3, and 10 ml of prescription 4, per injection was administered once every month for a total of four times. The observations were as shown in Table 4

(No. 4)

Prescriptions 1 and 3 were equally mixed and locally injected to an adiposis cell tumor of a large-size dog (male, weighing about 40 kg). A total amount of 3 ml, which consists of 1.5 ml of prescription 1 and 1.5 ml of prescription 3, per injection was administered once every month for a total of five times. The observations were as shown in Table 4

(No. 5)

Prescriptions 1 and 3 were equally mixed and locally injected to an adiposis cell tumor of a middle-size dog (female, weighing about 15 kg). A total amount of 0.8 ml, which consists of 0.4 ml of prescription 1 and 0.4 ml of prescription 3, per injection was administered once every month for a total of four times. The observations were as shown in Table 4
(No. 6)

Prescriptions 1 and 3 were equally mixed and locally injected to a trichoepithelioma of a small-size dog (female, weighing about 3 kg). A total amount of 5 ml, which consists of 2.5 ml of prescription 1 and 2.5 ml of prescription 3, per injection was administered once every month for a total of two times. The observations were as shown in Table 4
(No. 7)

Prescriptions 1 and 3 were equally mixed and locally injected to tongue cancer of a honey parrot (male, weighing about 0.4 kg). A total amount of 0.8 ml to 1 ml, which consists of 0.4 ml to 0.5 ml of prescription 1 and 0.4 ml to 0.5 ml of prescription 3, per injection was administered once every month for a total of five times. The observations were as shown in Table 4

TABLE 4

| No. | Observation Results |
| --- | --- |
| 1 | Tumor diameter reduced from 11.4 mm to 9 mm, volume reduced by ½ |
| 2 | Completely healed |
| 3 | Reduced to ⅙ by third month |
| 4 | Reduced and cut off, tumor did not occur again |
| 5 | Completely healed |
| 6 | Completely healed |
| 7 | Completely healed |

What is claimed is:

1. A local injection prescription produced by dissolving an organic compound having a lactone nucleus in lower alcohol and water and mixing with an α-amino acid, wherein the organic compound is a macrolide, and the macrolide is an avermectin.

2. The local injection prescription according to claim 1, wherein the lower alcohol is one selected from a group of alcohols represented by the molecular formulas of $CH_4O$, $C_2H_6O$, $C_3H_8O$, and $C_4H_{10}O$.

3. The local injection prescription according to claim 1, wherein the α-amino acid is theanine.

4. The local injection prescription according to claim 3 mixed with vitamin B6.

5. The local injection prescription according to claim 1, wherein the local injection prescription is injected directly to a lesion in which a tumor is situated.

6. A method of administering a local injection prescription for dispersing a malignant tumor in a lesion, the method comprising:

providing the local injection prescription, the local injection prescription produced by dissolving an organic compound having a lactone nucleus in lower alcohol and water, wherein the organic compound is a macrolide, and the macrolide is an avermectin; and injecting the local injection prescription to the lesion.

7. The method of claim 6, wherein the local injection prescription is injected directly to the lesion.

8. The method of claim 6, wherein the local injection prescription is mixed with an α-amino acid.

9. The method of claim 6, wherein the lower alcohol is one selected from a group of alcohols represented by the molecular formulas of $CH_4O$, $C_2H_6O$, $C_3H_8O$, and $C_4H_{10}O$.

10. The method of claim 8, wherein the α-amino acid is theanine.

11. The method of claim 6, wherein the local injection prescription is mixed with vitamin B6.

* * * * *